United States Patent
Arai et al.

[11] Patent Number: 6,162,806
[45] Date of Patent: Dec. 19, 2000

[54] ACTIVE OXYGEN SCAVENGERS CONTAINING PTERIN DERIVATIVES

[75] Inventors: Toshiyuki Arai; Keisuke Makino; Kenjiro Mori, all of Kyoto, Japan

[73] Assignee: Artemis, Inc., Tokyo, Japan

[21] Appl. No.: 09/051,054

[22] PCT Filed: Jul. 30, 1997

[86] PCT No.: PCT/JP97/02649

§ 371 Date: Mar. 31, 1998

§ 102(e) Date: Mar. 31, 1998

[87] PCT Pub. No.: WO98/04558

PCT Pub. Date: May 2, 1998

[30]     Foreign Application Priority Data

Jul. 31, 1996  [JP]  Japan .................................. 8-218043

[51] Int. Cl.[7] ...................... A61K 31/495; A61K 31/505; C07D 475/00
[52] U.S. Cl. .......................... 514/249; 514/256; 544/258
[58] Field of Search ............... 544/258; 514/249, 514/256

[56]     References Cited

FOREIGN PATENT DOCUMENTS

| 4418096 | 11/1995 | Germany . |
|---|---|---|
| 06056669 | 3/1994 | Japan . |
| WO98/08516 | 3/1998 | Japan . |
| WO 95/31987 | 11/1995 | WIPO . |
| 9603989 | 2/1996 | WIPO . |

OTHER PUBLICATIONS

Chem Abstracts 66:9261 1966.

*Primary Examiner*—Gary Geist
*Assistant Examiner*—Everett White

*Attorney, Agent, or Firm*—Sughrue, Mion, Zinn, Macpeak & Seas, PLLC

[57]     ABSTRACT

An active oxygen scavenger comprising as an active ingredient a pterin derivative of the formula (I):

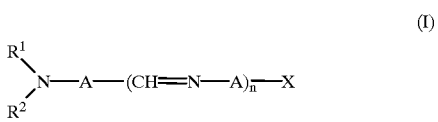

(I)

wherein $R^1$ and $R^2$ are independently a hydrogen atom, an alkyl group of 1 to 4 carbon atoms, or an acyl group of the formula $R^3$—CO—, $R^3$ is an alkyl group of 1 to 4 carbon atoms, X is a formyl group or hydroxymethyl group, A is a group of the formula (Ia):

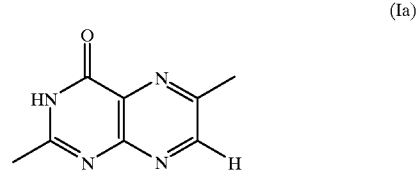

(Ia)

and n is 0 or an integer of 1 or more, with the proviso that when X is a hydroxymethyl group, n is 0, or when n is an integer of 1 or more, each of $R^1$ and $R^2$ is a hydrogen atoms, and X is a formyl group, or a cyclic compound thereof, or a salt thereof is disclosed.

10 Claims, 5 Drawing Sheets

ACTIVE OXYGEN SCAVENGERS CONTAINING PTERIN DERIVATIVES

This application is a 371 of PCT/JP97/02649, filed Jul. 30, 1997.

TECHNICAL FIELD

The present invention relates to an active oxygen scavenger containing a pterin derivative. Further, the present invention relates to a pharmaceutical or cosmetic composition containing the pterin derivative.

BACKGROUND ART

Various diseases which an active oxygen would be implicated in have been known from the past. Examples of such diseases are ischemic disorder (such as sequela of ischemic heart disease, sequela of cerebral infarction, or stress ulcers), reperfusion disorder, inflammatory disease (such as chronic rheumatism, nephritis, or asthma), cancer, diabetes, cataract, arteriosclerosis, drug toxinosis, pesticide toxinosis, hepatopathy caused by an excess administration of a drug or an excess taking up of a pesticide, retinopathy of prematurity, hyperesthesia optica, or disorder caused by radiation.

For the treatment of such diseases, administration of an enzyme exhibiting an active oxygen scavenging activity, for example, superoxide dismutase (hereinafter sometimes referred to as SOD) is considered effective. However, the half-life period of SOD in a living body is extremely short, and therefore, SOD should be administered in a large amount. When a long-term administration of SOD is required, it is necessary to take care of side effects, such as an anaphylactic shock caused by an antigen-antibody reaction, because the enzyme is a protein and has antigenecity. Further, there exist various problems, for example, in that no effect can be obtained from oral administration.

As one of non-protein compounds having the active oxygen scavenging activity, pterin derivatives are known. For example, Japanese Unexamined Patent Publication (Kokai) No. 6-56669 discloses that a pterin derivative or a neopterin derivative exhibits the active oxygen scavenging activity. Further, Japanese Unexamined Patent Publication (Kokai) No. 7-188232 discloses that the above-mentioned pterin derivative or neopterin derivative is effective against cytopathy caused by free radicals.

Neopterin (abbreviated to NP), i.e., 2-amino-4-oxo-6-(D-erythro-1',2',3'-trihydroxypropyl)-pteridine, is a typical compound of the above-mentioned pterin derivatives or neopterin derivatives and released from macrophages. Although the physiological functions of NP are not completely elucidated, it is known to have an antioxidative activity against active oxygens (for example, S. Kojima et al., FEBS, 304, 2, 3, 163–166, 1992; or S. Kojima et al., FEBS, 329, 1, 2, 125–128, 1993).

Further, it is known that 5,6,7,8-tetrahydroneopterin (abbreviated to NPH4), i.e., the reduced neopterin, has the potent antioxidative activity, and it is reported that NPH4 is effective against various diseases (for example, S. Kojima et al., FEBS, 304, 2, 3, 163–166, 1992; Icho et al., Biochemical Pharmacology, 45, 10, 1953–1958, 1993; or Arai et al., Neuroscience Letters, 173, 107–110, 1994).

Nevertheless, 5,6,7,8-tetrahydroneopterin (NPH4) exhibits teratogenicity, and therefore, a different non-protein compound having the active oxygen scavenging activity has been desired.

The inventors of the present invention engaged in intensive research to find non-protein compounds having the active oxygen scavenging activity, and as a result, found that a pterin derivative which has not been known to have the active oxygen scavenging activity actually exhibits such an activity. The present invention is based on the findings.

DISCLOSURE OF INVENTION

The object is achieved by the present invention relating to an active oxygen scavenger characterized by comprising as an active ingredient a pterin derivative of the formula (I):

(I)

wherein $R^1$ and $R^2$ are independently a hydrogen atom, an alkyl group of 1 to 4 carbon atoms, or an acyl group of the formula $R^3$—CO—, $R^3$ is an alkyl group of 1 to 4 carbon atoms, X is a formyl or hydroxymethyl group, A is a group of the formula (Ia):

(Ia)

and n is 0 or an integer of 1 or more, with the proviso that when X is a hydroxymethyl group, n is 0, or when n is an integer of 1 or more, each of $R^1$ and $R^2$ is a hydrogen atom, and X is a formyl group, or a cyclic compound thereof, or a salt thereof.

Further, the present invention relates to a pharmaceutical composition characterized by comprising as an active ingredient the pterin derivative of the formula (I), or a cyclic compound thereof, or a pharmaceutically acceptable salt thereof.

Furthermore, the present invention relates to a cosmetic composition characterized by comprising as an active ingredient the pterin derivative of the formula (I), or a cyclic compound thereof, or a salt thereof.

BEST MODE FOR CARRYING OUT THE INVENTION

The present invention will be explained in detail hereinafter.

The active oxygen scavenger of the present invention contains the pterin derivative of the formula (I) as an active ingredient.

The alkyl group of 1 to 4 carbon atoms for $R^1$, $R^2$, and $R^3$ means a straight or branched alkyl group of 1 to 4 carbon atoms, for example, a methyl, ethyl, n-propyl, i-propyl, n-butyl, i-butyl, sec-butyl, or tert-butyl group. A preferable group is a methyl or ethyl group. In the compound of the formula (I), $R^1$ and $R^2$, which may be same or different, are independently a hydrogen atom, an alkyl group of 1 to 4 carbon atoms, or an acyl group of the formula $R^3$—CO—, wherein $R^3$ is an alkyl group of 1 to 4 carbon atoms. In the formula (I), n is 0 or an integer of 1 or more, preferably 0 or an integer of 1 to 100, more preferably 0 or an integer of 1 to 10.

A preferable pterin derivative is a 6-formyl-pterin derivative of the formula (I) wherein $R^1$ and $R^2$ are independently a hydrogen atom, an alkyl group of 1 to 4 carbon atoms, or an acyl group of the formula $R^3$—CO—, $R^3$ is an alkyl group of 1 to 4 carbon atoms, A is a group of the formula (Ia), n is 0 or an integer of 1 or more, and X is a formyl group.

A more preferable pterin derivative is the compound of the formula (I) wherein $R^1$ and $R^2$ are hydrogen atoms, and n is 0, i.e., 6-formyl-pterin of the formula (II):

(II)

Because 6-formyl-pterin has an amino group and a formyl group, plural molecules thereof spontaneously produce Schiff bases in an aqueous solution to form 6-formyl-pterin oligomers or polymers. The oligomer or polymer may be not only a straight oligomer or polymer, but also a cyclic oligomer or polymer. The reaction from the monomers to the oligomer or polymer is reversible. Under alkaline conditions, the 6-formyl-pterin oligomer or polymer is easily cleaved to form the 6-formyl-pterin monomers. Therefore, the same reversible reaction will occur in a living body or on the surface of skin. The 6-formyl-pterin oligomer or polymer is a compound of the formula (I) wherein $R^1$ and $R^2$ are hydrogen atoms at the same time, and n is an integer of 1 or more, preferably 1 to 100, and may be used as the active ingredient in the active oxygen scavenger of the present invention.

A derivative which may be easily converted to the pterin derivative of the formula (I), i.e., a prodrug, may be used as the active ingredient of the invention. A method generally used for selecting and preparing an appropriate prodrug is disclosed in, for example, Design of Prodrugs, ed. H. Bundgaard, Elsevier, 1985.

6-Formyl-pterin may be used as the active ingredient in the form of a free compound, or a salt thereof, particularly a pharmaceutically acceptable salt thereof, for example, a salt of an inorganic acid, such as hydrochloride or sulfate, or a salt of an organic acid, such as camphor sulfonate, tartarate, malate, or oxalate. Further, 6-formyl-pterin may be used in the form of the oligomer or polymer. The 6-formyl-pterin oligomer or polymer is a known compound and may be converted from a free compound to a salt thereof, from a salt to a free compound, or from a salt to a different salt, in accordance with methods which are in themselves known.

The pterin derivative of the formula (I) may be also used as the active ingredient in the form of a free compound, or a salt thereof, particularly a pharmaceutically acceptable salt thereof, for example, a salt of an inorganic acid, such as hydrochloride or sulfate, or a salt of an organic acid, such as camphor sulfonate, tartarate, malate, or oxalate. The pterin derivative of the formula (I) is a known compound and may be prepared in accordance with methods which are in themselves known. The pterin derivative of the formula (I) may be converted from a free compound to a salt thereof, from a salt to a free compound, or from a salt to a different salt, in accordance with methods which are in themselves known.

The pterin derivative of the formula (I), or the cyclic compound thereof, or the pharmaceutically acceptable salt thereof exhibits the active oxygen scavenging activity or may be converted to a compound exhibiting the active oxygen scavenging activity, and therefore, it may be used as the active ingredient of the pharmaceutical composition of the present invention.

The pterin derivative of the formula (I) wherein n is 0 and one of $R^1$ and $R^2$ is not a hydrogen atom, or 6-formyl-pterin, i.e., the compound of the formula (I) wherein n is 0, $R^1$ and $R^2$ are hydrogen atoms at the same time, and X is a formyl group, per se, exhibits the active oxygen scavenging activity. Therefore, it is effective against active oxygens generated by various causes, regardless of systems wherein active oxygens are formed.

The pterin derivative of the formula (I) wherein n is an integer of 1 or more, particularly an integer of 1 to 100, may be slowly degraded to release 6-formyl-pterin in the body or on the surface of the body of an animal to which it is administered. Therefore, it is effective against active oxygens generated by various causes regardless of systems wherein active oxygens are formed.

Accordingly, the pharmaceutical composition of the present invention may be used to effectively treat or prevent various diseases which an active oxygen or radical is implicated in, for example, ischemic disorder (such as sequela of ischemic heart disease, sequela of cerebral infarction, or stress ulcers), reperfusion disorder, inflammatory disease (such as chronic rheumatism, nephritis, or asthma), cancer, diabetes, cataract, arteriosclerosis, drug toxinosis, pesticide toxinosis, hepatopathy by an excess administration of a drug or an excess taking up of a pesticide, retinopathy of prematurity, hyperesthesia optica, or disorder caused by radiation.

It is possible to administer the pharmaceutical composition according to the present invention, i.e., the pterin derivative or the pharmaceutically acceptable salt thereof, alone or preferably together with a pharmaceutically or veterinarily acceptable ordinary carrier, to an animal, preferably a mammal, particularly humans.

The formulation is not limited to, but may be, for example, oral medicines, such as powders, fine subtilaes, granules, tablets, capsules, suspensions, emulsions, syrups, extracts or pills, or parenteral medicines, such as injections, liquids for external use, ointments, suppositories, creams for topical application, jellys, gels, pastes, or eye lotions.

The oral medicines may be prepared by an ordinary method using, for example, fillers, binders, disintegrating agents, surfactants, lubricants, flowability-enhancers, diluting agents, preservatives, coloring agents, perfumes, tasting agents, stabilizers, humectants, antiseptics, antioxidants, or the like, such as gelatin, sodium alginate, starch, corn starch, saccharose, lactose, glucose, mannitol, carboxylmethylcellulose, dextrin, polyvinyl pyrrolidone, crystalline cellulose, soybean lecithin, sucrose, fatty acid esters, talc, magnesium stearate, polyethylene glycol, magnesium silicate, silicic anhydride, or synthetic aluminum silicate. For example, the capsule may be prepared by mixing and filling 6-formyl-pterin and lactose.

For the parenteral administration, for example, a topical application in the form of a cream or ointment, an injection such as a subcutaneous or intravenous injection, or the per rectum administration may be used. Of the parenteral formulations, an injection is preferably used.

When the injections are prepared, for example, water-soluble solvents, such as physiological saline or Ringer's solution, water-insoluble solvents, such as plant oil or fatty acid ester, tonicity agents, such as glucose or sodium chloride, solubilizing agents, stabilizing agents, antiseptics, suspending agents, emulsifying agents or the like may be optionally used, in addition to the pterin derivative as the active ingredient.

The pharmaceutical composition may be administered in the form of a sustained release preparation using sustained release polymers. For example, the pharmaceutical composition of the present invention may be incorporated into a pellet made of ethylenevinyl acetate polymers, and the pellet may be surgically implanted in a tissue to be treated.

The amount of the pterin derivative or the pharmaceutically acceptable salt thereof contained in the pharmaceutical composition of the present invention is not limited, but the pharmaceutical composition may contain 0.01 to 99%, preferably 0.1 to 80% by weight of the pterin derivative or the pharmaceutically acceptable salt thereof.

When the active oxygen scavenging activity is utilized, the dose of the pharmaceutical composition of the present invention varies with the kind of disease, the age, sex, body weight, symptoms, method of administration, or the like, but the pterin derivative may be orally or parenterally administered at a dosage of about 0.1 mg to 100 mg (calculated as 6-formyl-pterin) a day for an adult, usually once or divided into up to four dosages.

The pterin derivative of the formula (I), or the cyclic compound thereof, or the pharmaceutically acceptable salt thereof exhibits the active oxygen scavenging activity or may be converted to a compound exhibiting the active oxygen scavenging activity, and thus may be used as the active ingredient of the cosmetic composition of the present invention. Because skin is on the outermost layer of a living body, it is affected by an active oxygen generated by environmental factors, particularly the action of ultraviolet light. As dermatopathy affected by an active oxygen, there may be mentioned, for example, inflammatory dermatopathy, collagen disease, keratosis, hydroa, or hyperesthesia optica. It is known that keratin of skin functions as a barrier, and therefore, when agents for external use, such as cosmetics, are administered, the active ingredient acts mainly on the surface of skin, and thus, effectively suppresses, for example, peroxidation of lipids on the surface of skin. Accordingly, the cosmetic composition of the present invention can scavenge active oxygens which may be generated on the surface of skin by the action of ultraviolet light, radiation, nitrogen dioxide, or cigarette smoke to avoid, reduce, or prevent skin damage caused by the active oxygens.

The amount of the pterin derivative of the formula (I), or the cyclic compound thereof, or the salt thereof contained in the cosmetic composition of the present invention is not limited, but the cosmetic composition may contain 0.01 to 99%, preferably 0.1 to 80% by weight of the pterin derivative of the formula (I), or the cyclic compound thereof, or the salt thereof.

In addition to the active ingredient, the cosmetic composition of the present invention may optionally contain one or more other ingredients ordinarily used for cosmetics, for example, oils, antioxidants, surfactants, humectants, perfumes, water, alcohols, thickeners, antiseptics, mildew-proofing agents, coloring agents, powders, and/or medicines. Further, the cosmetic composition of the present invention may optionally contain, if necessary, well-known ultraviolet light absorbers, for example, benzoic acid-based ultraviolet light absorbers (such as p-aminobenzoic acid), anthranilic acid-based ultraviolet light absorbers (such as homomethyl-N-acetylanthranilate), salicylic acid-based ultraviolet light absorbers (such as amylsalicylate), cinnamic acid-based ultraviolet light absorbers (such as octyl cinnamate), and/or benzophenone-based ultraviolet light absorbers (such as 2,4-dihydroxybenzophenone).

The cosmetic composition of the present invention may be in the form of, for example, solutions, emulsions, pasty mixtures, solids (pressed solids), powders, or the like. The cosmetic composition of the present invention may be used as, for example, tanners, sun-blocking cosmetics, make-up bases, packs, lotions, foundations, creams, emulsions, shampoos, rinses, hair cosmetics, or the like. As described above, an excess of active oxygens may be generated under strong ultraviolet light, and therefore, it is preferable to use the cosmetic composition of the present invention as tanners or sun-blocking cosmetics for use under strong ultraviolet light, for example, sun oils, sun lotions, sunsceeens, sun-blocking creams, sun-blocking lotions, sun-blocking foundations, sun-blocking make-up bases, or sun-blocking hair tonics.

Acute toxicity of 6-formyl-pterin was examined, using rats. After 6 mg/kg (body weight) of 6-formyl-pterin was administered intravenously to 10 rats, the conditions of them were observed for 3 months. No death was observed.

The active oxygen scavenger of the present invention may be used not only for the pharmaceutical or cosmetic application but also for various applications, for example, as food such as a functional food or health food, as a feed for non-human animals, particularly breeding animals, or as an additive for a solution to preserve an organ to be transplanted.

EXAMPLES

The present invention now will be further illustrated by, but is by no means limited to, the following Examples.

Example 1

Measurement of Active Oxygen Scavenging Activity of 6-formyl-pterin (PMN-PMA system)

Venous blood (10 ml) was taken from a healthy adult, and polymorphonuclear leukocytes (abbreviated to PMN) were isolated therefrom. The leukocytes were suspended in HBSS (Hanks' balanced salt solution) to approximately $1 \times 10^6$ cells/ml. 2-Methyl-6-phenyl-3,7-dihydroimidazo-(1,2-a)-pyrazin-3-on (hereinafter referred to as CLA) as a chemiluminescent compound, that is, a compound which may generate chemiluminescence due to the presence of active oxygens, was dissolved in a phosphate buffered saline (hereinafter referred to as PBS) to the concentration of 50 μM. Phorbol myristate acetate (abbreviated to PMA) as a polymorphonuclear leukocyte stimulating agent, that is, a compound which may generate active oxygens by stimulating polymorphonuclear leukocytes, was dissolved in PBS to the concentration of 20 μg/ml. The PMN suspension, the CLA solution, and the PMA solution were cooled with ice for storage until use for measurement.

6-Formyl-pterin as the active ingredient of the active oxygen scavenger according to the present invention was dissolved in PBS to the concentrations of 100 μM, 250 μM, or 500 μM, and then warmed to 37° C. before measurement. PBS as a control was also warmed to 37° C. before measurement.

The measurement was performed as follows:

To polymorphonuclear leukocytes isolated from 2 ml of the PMN suspension by centrifugation, the 6-formyl-pterin solutions of various concentrations or PBS were added to adjust total volume to 1930 μl. The mixtures were poured into test tubes and warmed at 37° C. for 15 minutes. After adding the CLA solution (50 μl), the mixture was placed in a chemiluminescence reader and the measurement of an amount of chemiluminescence was started. After 1 minute from the beginning of the measurement, the PMA solution (20 μl) was injected into the test tube with a syringe. The measurement was performed at 37° C. for approximately 10 minutes while monitoring every 10 seconds.

Figure 1:
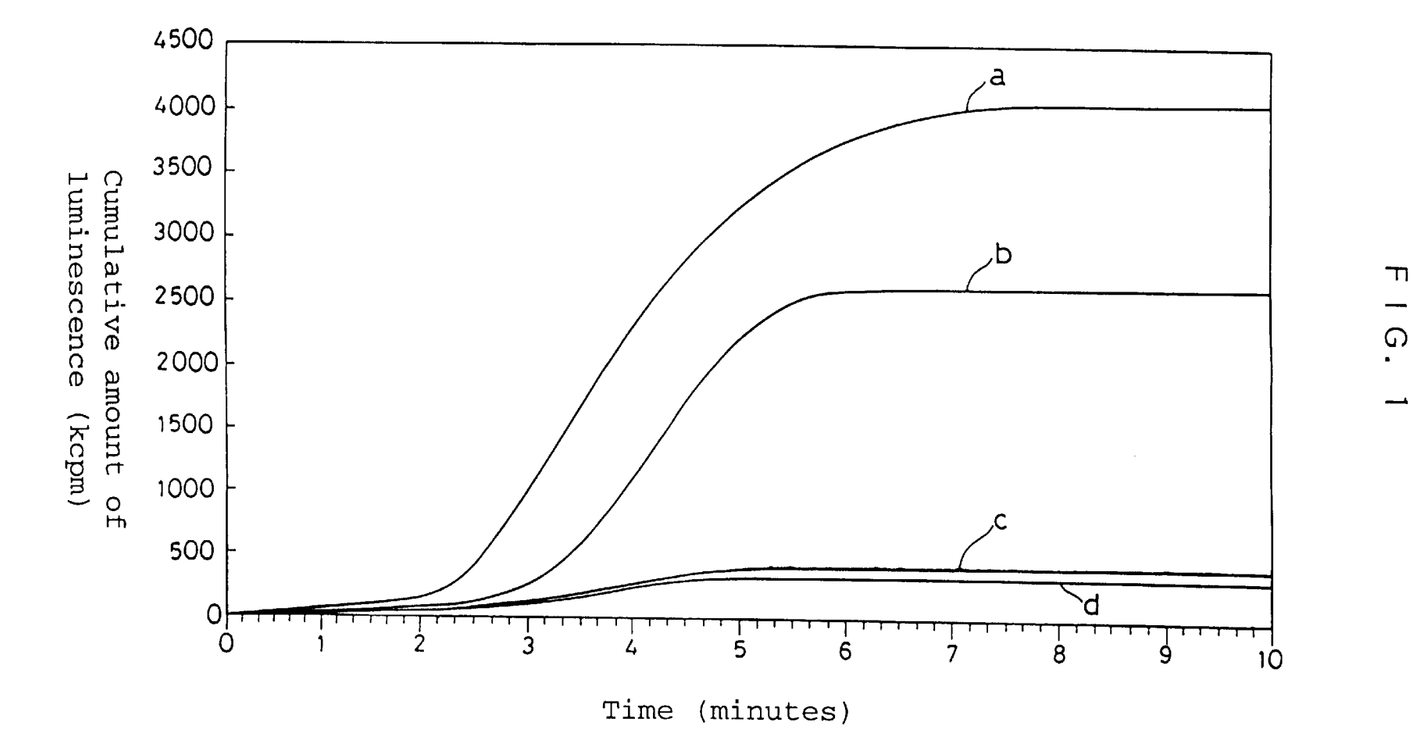
FIG. 1 is a graph showing a cumulative amount of luminescence as the active oxygen scavenging activity of 6-formyl-pterin in PMN-PMA system.

The results are shown in FIG. 1. FIG. 1 is a graph showing a total chemiluminescence amount obtained by accumulating chemiluminescence amounts measured every 10 seconds. In FIG. 1, the curve a shows the result of the control test wherein only PBS was added instead of 6-formyl-pterin, the curve b shows the result of the test wherein 100 μM of 6-formyl-pterin was added, the curve c shows the result of the test wherein 250 μM of 6-formyl-pterin was added, and the curve d shows the result of the test wherein 500 μM of 6-formyl-pterin was added. In comparison with the control test wherein only PBS was added instead of 6-formyl-pterin (the curve a), the amount of chemiluminescence, i.e., the amount of active oxygens, was significantly suppressed, in the test wherein 100 μM of 6-formyl-pterin was added (the curve b), and further, the amount of chemiluminescence, i.e., the amount of active oxygens almost disappeared in the tests wherein 250 μM of 6-formyl-pterin (the curve c) or 500 μM of 6-formyl-pterin (the curve d) was added.

Example 2

Measurement of Active Oxygen Scavenging Activity of 6-formyl-pterin (active oxygen derived from potassium superoxide)

Potassium superoxide ($KO_2$) (28 mg) was added to dimethyl sulfoxide (DMSO) (20 ml) to prepare a saturated solution so that active oxygens were generated in DMSO. As a standard substance, 2,2,6,6-tetramethylpiperidine-N-oxide (TEMPO) was used. TEMPO was dissolved in DMSO in the concentrations of 0.1, 0.3, 0.5, 0.7, 1, 1.2, or 1.5 mM. The electron spin resonance signals obtained (measured at 77K) were integrated to prepare a standard curve. The concentration of active oxygens in DMSO was determined by comparing the standard curve to be approximately 0.5 mM.

6-Formyl-pterin as the active ingredient of the active oxygen scavenger according to the present invention was dissolved in DMSO in the concentration of 10 mM. The amount of active oxygens generated in the absence of 6-formyl-pterin in the $KO_2$ solution (control), and the amount of active oxygens generated in the presence of predetermined concentrations of 6-formyl-pterin were measured by the liquid He temperature (77K) electron spin resonance spectroscopy, respectively.

Figure 2:
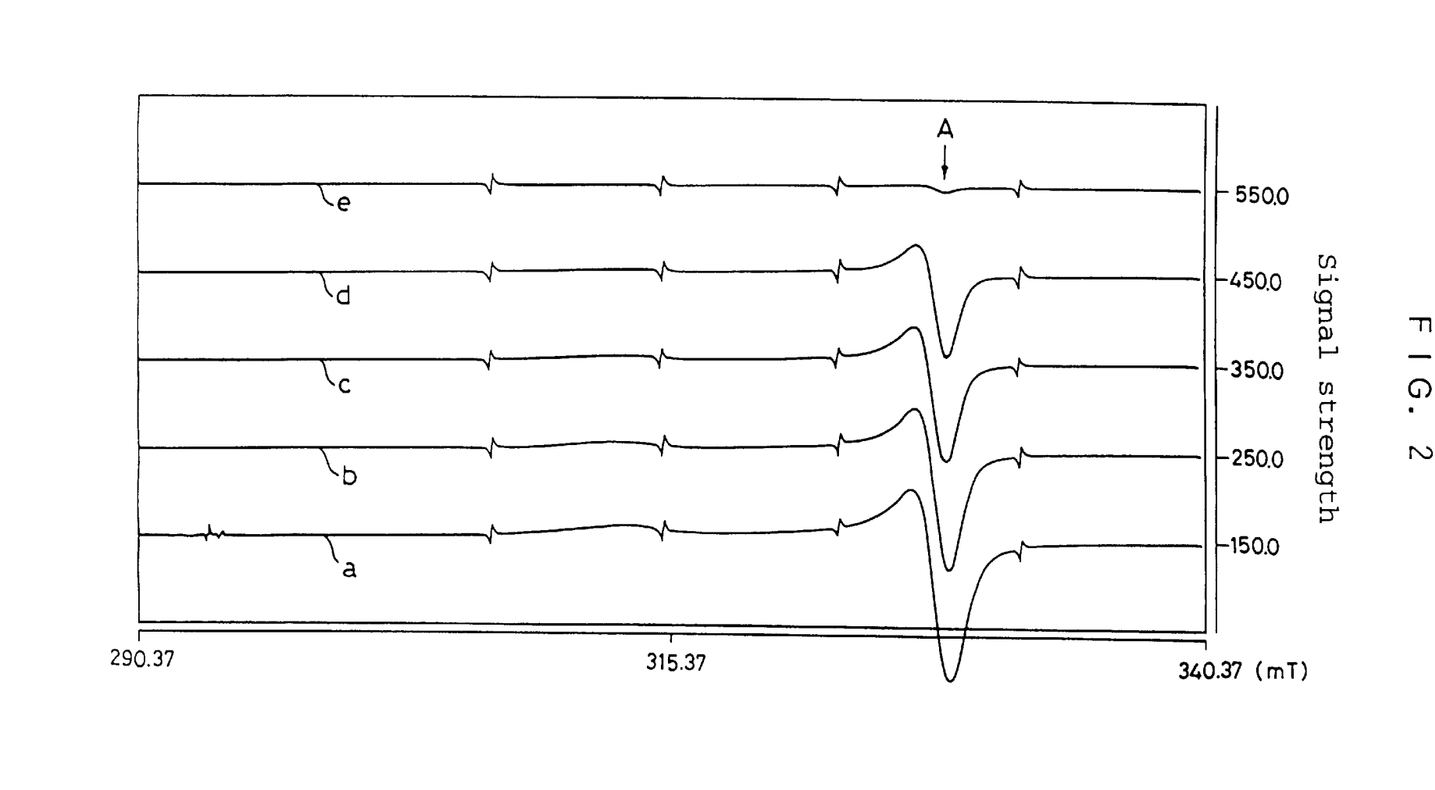
FIG. 2 is a graph showing the results of the measurement by the liquid He temperature election spin resonance spectroscopy, when 6-formyl-pterin was added to a DMSO solution of potassium superoxide.

The results are shown in FIG. 2. The amount of active oxygens generated from $KO_2$ when the final concentrations of 6-formyl-pterin in DMSO were raised from 0.001 mM to 1 mM in a graduated manner by 10 times can be determined from the value calculated by integrating twice a peak (first-derivative spectrum) at the position of arrow A, i.e., the position of 328 mT. In FIG. 2, the curve a shows the result when 6-formyl-pterin was not added (control), and the curves b to e show the results when 0.001 mM, 0.01 mM, 0.1 mM, and 1 mM of 6-formyl-pterin was added, respectively.

When 6-formyl-pterin was added to the $KO_2$ solution, in comparison with the case that 6-formyl-pterin was not added to the $KO_2$ solution, the amount of active oxygens generated from $KO_2$ was lowered from 0.1 mM 6-formyl-pterin, and the amount of active oxygens generated from $KO_2$ almost disappeared at 1 mM 6-formyl-pterin.

As confirmed above, the amount of active oxygens generated from the system wherein $KO_2$ (28 mg) was added to DMSO (20 ml) was approximately 0.5 mM. Accordingly, the results show that 6-formyl-pterin scavenged active oxygens generated from $KO_2$ in a ratio of approximately 1:1.

Example 3

Measurement of Active Oxygen Scavenging Activity of a Hydroxymethyl Derivative (active oxygen derived from potassium superoxide)

The procedure described in Example 2 was repeated, except that 0.01 mM to 10 mM of 6-hydroxymethyl-pterin [i.e., a compound of the formula (I) wherein $R^1$ and $R^2$ are hydrogen atoms, X is a hydroxymethyl group, and n is 0] was used instead of 0.001 mM to 1 mM of 6-formyl-pterin, to find that the active oxygen scavenging activity of 6-hydroxymethyl-pterin was the same as that of 6-formyl-pterin when the concentration of 6-hydroxymethyl-pterin was 10 times that of 6-formyl-pterin.

Example 4

Suppression of Delayed Neuronal Death, by Active Oxygen Scavenging Activity

A neck of each gerbil (body weigh=approximately 80 g) under a general anesthesia was incised. Ambilateral carotids were visually ligated with clips to cut off a bloodstream. After 5 minutes, the bloodstream was resumed, and the incision was sutured. After 30 minutes from the resumption of the bloodstream, physiological saline (1 ml) was intraperitoneally administered to a control group of the gerbils, whereas 50 mM of 6-formyl-pterin in physiological saline (1 ml) was intraperitoneally administered to an administering group of the gerbils. Thereafter, gerbils came out from anesthesia and then were bred for 1 week. Then, a brain was extirpated from each gerbil under a general anesthesia. Tissue slices were prepared from the brain and stained with microtubule-associated protein 2 (MAP2) which can specifically stain neurons, to evaluate the degree of delayed neuronal death (DND) in the cerebral hippocampus area.

Figure 3:
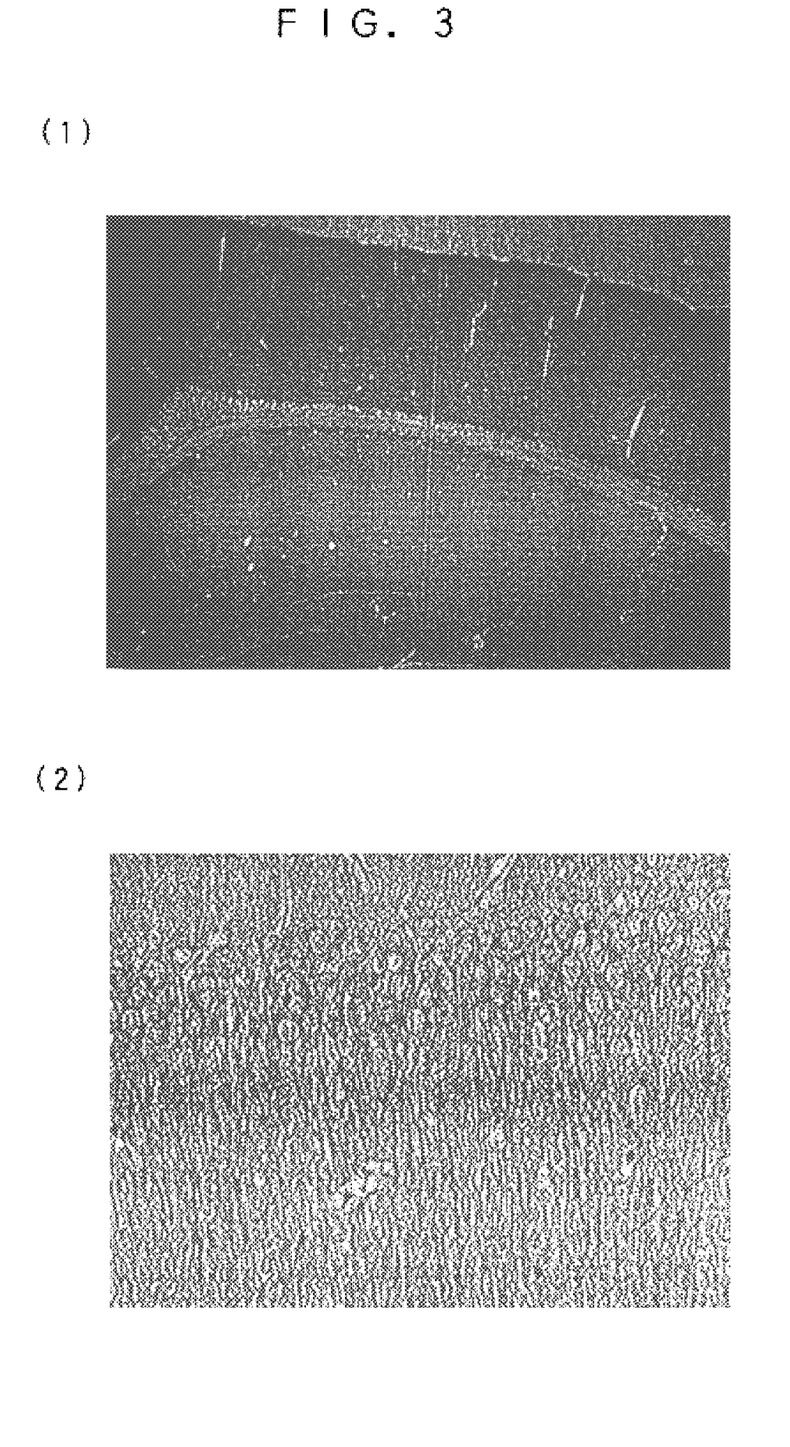
FIG. 3 is a photomicrograph of a slice of a cerebral hippocampus tissue from a completely normal gerbil which had not encountered hemostasis.
Figure 4:
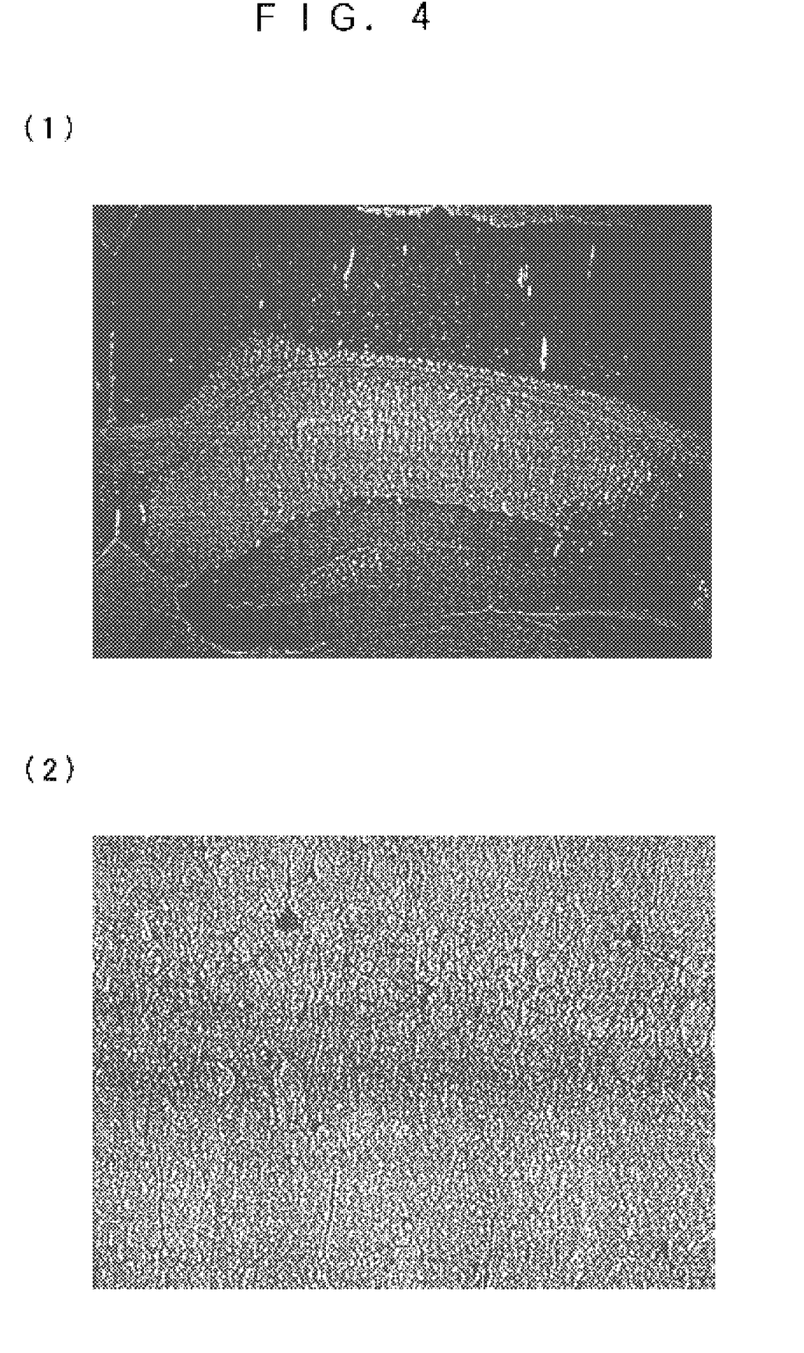
FIG. 4 is a photomicrograph of a slice of a cerebral hippocampus tissue from the control group of gerbils which had suffered from transient cerebral ischemia.
Figure 5:
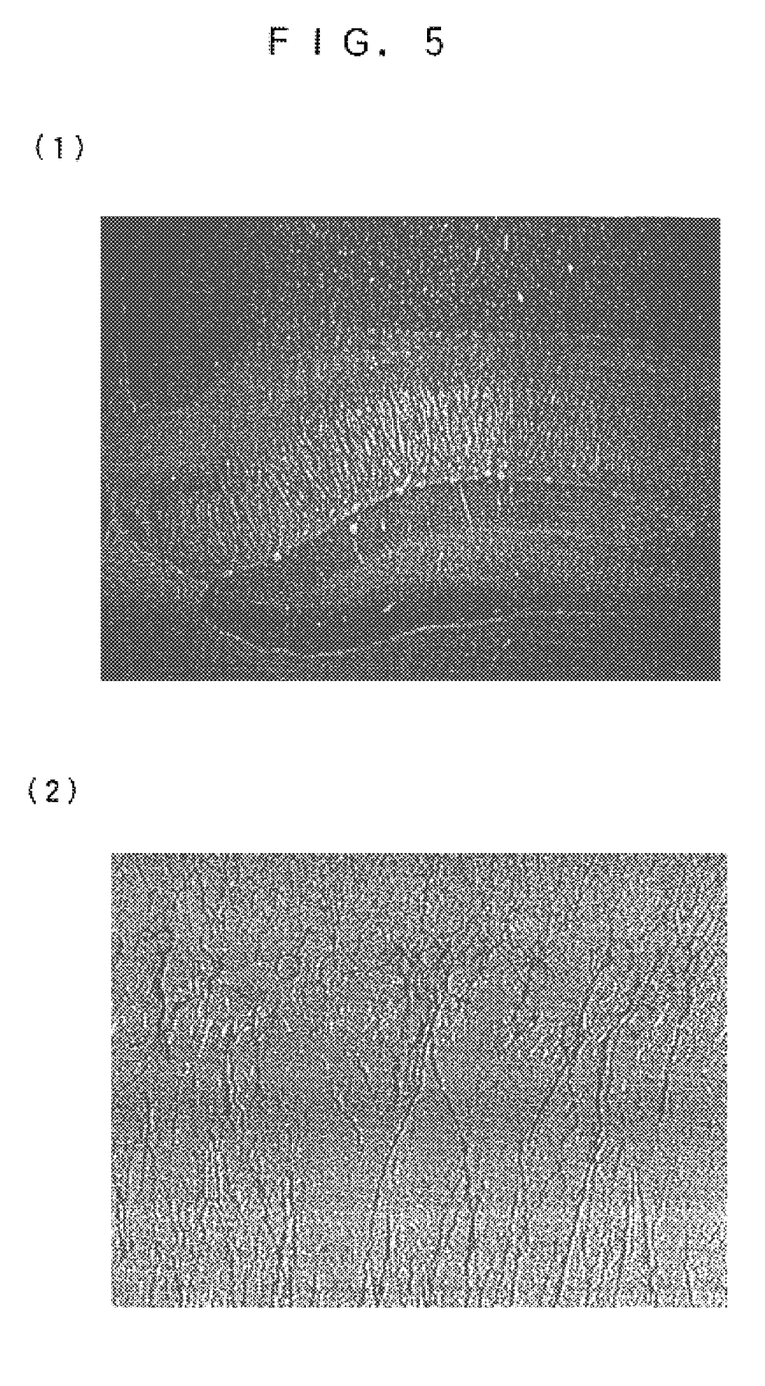
FIG. 5 is a photomicrograph of a slice of a cerebral hippocampus tissue from the 6-formyl-pterin-administering group of the transient cerebral ischemia model gerbils.

Photomicrographs of the tissue slices of the cerebral hippocampus area of the gerbils are shown in FIGS. 3 to 5. FIG. 3 is a photomicrograph of a slice of a cerebral hippocampus tissue from a completely normal gerbil which had not encountered hemostasis, FIG. 4 is a photomicrograph of a slice of a cerebral hippocampus tissue from the control group, and FIG. 5 is a photomicrograph of a slice of a cerebral hippocampus tissue from the 6-formyl-pterin-administering group. FIG. 3(1), FIG. 4(1), and FIG. 5(1) are photomicrographs having a magnification of approximately ×60, and FIG. 3(2), FIG. 4(2), and FIG. 5(2) are photomicrographs having a magnification of approximately ×600.

FIG. 4 shows the state where neurons were completely dropped, and FIG. 5 shows the state where many neurons were living. These results show that delayed neuronal death was suppressed by the active oxygen scavenging activity of 6-formyl-pterin in the gerbils which had suffered from the transient cerebral ischemia.

INDUSTRIAL APPLICABILITY

The active oxygen scavenger of the present invention is widely effective against active oxygens generated by various causes. Therefore, the pharmaceutical composition of the present invention containing the active oxygen scavenger are expected to effectively treat various diseases which an active oxygen would be implicated in. Further, the cosmetic composition of the present invention containing the active oxygen scavenger are expected to reduce or avoid adverse influence of active oxygens generated by the action of ultraviolet light or the like.

What is claimed is:

1. A composition containing:

an active oxygen scavenger comprising as an active ingredient a pterin derivative of the formula (I):

(I)

wherein $R^1$ and $R^2$ are independently a hydrogen atom, an alkyl group of 1 to 4 carbon atoms, or an acyl group of the formula $R^3$—CO—, $R^3$ is an alkyl group of 1 to 4 carbon atoms, X is a formyl group, A is a group of the formula (Ia):

(Ia)

and n is 0 or an integer of 1 or more, with the proviso that when n is an integer of 1 or more, each of $R^1$ and $R^2$ is a hydrogen atom;

or a pharmaceutically acceptable salt of a compound of the formula (I); and a pharmaceutically or veterinarily acceptable carrier.

2. The composition according to claim 1, wherein the pterin derivative of the formula (I) is 6-formyl-pterin of the formula (II):

(II)

or a salt of the 6-formyl-pterin of the formula (II).

3. A cosmetic composition containing:

an active oxygen scavenger comprising as an active ingredient the pterin derivative of the formula (I), (I)

wherein $R^1$ and $R^2$ are independently a hydrogen atom, an alkyl group of 1 to 4 carbon atoms, or an acyl group of the formula $R^3$—CO—, $R^3$ is an alkyl group of 1 to 4 carbon atoms, X is a formyl group, A is a group of the formula (Ia):

(Ia)

and n is 0 or an integer of 1 or more, with the proviso that when n is an integer of 1 or more, each of $R^1$ and $R^2$ is a hydrogen atom;

or a salt of a compound of the formula (I); and an ingredient ordinarily used for cosmetics.

4. The cosmetic composition according to claim 3, wherein the pterin derivative of the formula (I) is 6-formyl-pterin of the formula (II):

(II)

or a salt of the 6-formyl-pterin of the formula (II).

5. A functional food for preventing or treating reperfusion disorder, said functional food containing:

an active oxygen scavenger comprising the pterin derivative of the formula (I):

(I)

wherein $R^1$ and $R^2$ are independently a hydrogen atom, an alkyl group of 1 to 4 carbon atoms, or an acyl group of the formula R³—CO—, R³ is an alkyl group of 1 to 4 carbon atoms, X is a formyl group, A is a group of the formula (Ia):

(Ia)

and n is 0 or an integer of 1 or more, with the proviso that when n is an integer of 1 or more, each of R¹ and R² is a hydrogen atom;
or a salt of a compound of the formula (I).

6. The functional food according to claim 5, wherein the pterin derivative of the formula (I) is 6-formyl-pterin of the formula (II):

(II)

or a salt of the 6-formyl-pterin of the formula (II).

7. A liquid to preserve an organ, said liquid containing an oxygen scavenging additive comprising:
the pterin derivative of the formula (I)

(I)

wherein R¹ and R² are independently a hydrogen atom, an alkyl group of 1 to 4 carbon atoms, or an acyl group of the formula R³—CO—, R³ is an alkyl group of 1 to 4 carbon atoms, X is a formyl group, A is a group of the formula (Ia):

(Ia)

and n is 0 or an integer of 1 or more, with the proviso that when n is an integer of 1 or more, each of R¹ and R² is a hydrogen atom; or a salt of a compound of the formula (I).

8. The liquid to preserve an organ according to claim 7, wherein the pterin derivative of the formula (I) is 6-formyl-pterin of the formula (II):

(II)

or a salt of the 6-formyl-pterin of the formula (II).

9. A method for preventing or treating a disease in which superoxide or an active oxygen from polymorphonuclear leucocyte is implicated, comprising administering to a mammal in need thereof an active oxygen scavenger comprising:

the pterin derivative of the formula (I)

(I)

wherein R¹ and R² are independently a hydrogen atom, an alkyl group of 1 to 4 carbon atoms, or an acyl group of the formula R³—CO—, R³ is an alkyl group of 1 to 4 carbon atoms, X is a formyl group, A is a group of the formula (Ia):

(Ia)

and n is 0 or an integer of 1 or more, with the proviso that when n is an integer of 1 or more, each of R¹ and R² is a hydrogen atom; or a salt of a compound of the formula (I).

10. The method according to claim 9, wherein the disease in which an active oxygen is implicated is reperfusion disorder.

* * * * *

UNITED STATES PATENT AND TRADEMARK OFFICE
CERTIFICATE OF CORRECTION

PATENT NO. : 6,162,806
DATED : December 19, 2000
INVENTOR(S) : Toshiyuki Arai, Keisuke Makino, Mori Kenjiro It is certified that error appears in the above-identified patent and that said Letters Patent is hereby corrected as shown below:

Title page,
Item [87] PCT Pub. Date, delete "May 2, 1998" and insert -- February 5, 1998 --.

Signed and Sealed this

Thirtieth Day of October, 2001

*Attest:*

*Attesting Officer*

NICHOLAS P. GODICI
*Acting Director of the United States Patent and Trademark Office*